United States Patent [19]

Davis et al.

[11] Patent Number: 5,611,800

[45] Date of Patent: Mar. 18, 1997

[54] SPINAL FIXATION SYSTEM

[75] Inventors: Bradford D. Davis, Rancho Mirage; Mike Stednitz, Indio; Mark Urbanski, La Quinta, all of Calif.

[73] Assignee: Alphatec Manufacturing, Inc., Palm Desert, Calif.

[21] Appl. No.: 196,448

[22] Filed: Feb. 15, 1994

(Under 37 CFR 1.47)

[51] Int. Cl.[6] ........................................... A61B 17/70
[52] U.S. Cl. ........................ 606/61; 606/72; 606/73
[58] Field of Search ................... 606/61, 60, 59, 606/54, 72, 73, 90, 105; 623/17

[56] References Cited

U.S. PATENT DOCUMENTS

| | | |
|---|---|---|
| 4,662,365 | 5/1987 | Gotzen et al. . |
| 4,790,297 | 12/1988 | Luque . |
| 4,913,134 | 4/1990 | Luque . |
| 4,946,458 | 8/1990 | Harms et al. . |
| 4,987,892 | 1/1991 | Krag et al. ........................... 606/61 |
| 5,002,542 | 3/1991 | Frigg ..................................... 606/61 |
| 5,047,029 | 9/1991 | Aebi et al. . |
| 5,084,049 | 1/1992 | Asher et al. . |
| 5,092,893 | 3/1992 | Smith ................................... 623/17 |
| 5,108,395 | 4/1992 | Laurain . |
| 5,127,912 | 7/1992 | Ray et al. . |
| 5,129,900 | 7/1992 | Asher et al. ....................... 606/61 |
| 5,181,917 | 1/1993 | Rogozinski ....................... 606/61 |
| 5,209,752 | 5/1993 | Ashman et al. ................... 606/61 |
| 5,234,431 | 8/1993 | Keller ................................. 606/70 |
| 5,261,907 | 11/1993 | Vignaud et al. . |
| 5,261,909 | 11/1993 | Sutterlin et al. ................. 606/61 |
| 5,282,801 | 2/1994 | Sherman . |
| 5,306,309 | 4/1994 | Wagner et al. ................... 623/17 |
| 5,334,203 | 8/1994 | Wagner . |
| 5,344,421 | 9/1994 | Crook ................................. 606/61 |
| 5,380,325 | 1/1995 | Lahille et al. ..................... 606/61 |

FOREIGN PATENT DOCUMENTS

| | | |
|---|---|---|
| 140329 | 2/1980 | Germany . |
| 3219575A1 | 5/1982 | Germany . |
| 3219575C2 | 5/1982 | Germany . |
| 780652 | 8/1957 | United Kingdom . |
| 2090745 | 7/1982 | United Kingdom . |

OTHER PUBLICATIONS

Pierre Compte, "Metallurgical Observations Of Biomaterials", *Contempory Biomaterials, Boretos ed. Noyes Publications, Park Ridge, New Jersey*, pp. 66–91 (1984).

"TSRH Spinal Design Rationale", pp. 1–11. *Danek Group, Inc.* (1992) Memphis. TN.

Excerpts from "TSRH Crosslink™", *Surgical Technique Manual*, pp. 1–2, 4–8, Danek Medical, Inc. Memphis, TN.

Moss, Excerpts from "Titanium–Mesh–Cylinder", West Germany, 2 pages, date unknown.

(List continued on next page.)

*Primary Examiner*—Guy V. Tucker
*Attorney, Agent, or Firm*—Knobbe Martens Olsen & Bear

[57] ABSTRACT

A spinal fixation system comprised of a bone mounting device, a support rod, and an attachment assembly interconnecting the bone mounting device to the support rod. The bone mounting device can include either bone screws configured to be screwed into the pedicle region of a vertebral body in the patient or hook mounting devices configured to be hooked around a portion of a vertebral body. The bone mounting devices include a multi-faceted connecting surface which is generally a crosshatched surface. The attachment assembly includes a housing having two openings for the support rod and a cam core member which has an eyebolt opening which is positioned in the housing so the support rod extends through the housing openings and the eyebolt opening. The cam core member also has a shaft on which the bone mounting device is positioned as well as a locking cap. The locking cap secures the bone mounting member to the shaft with the first multi-faceted connecting surface interlocking with a second multi-faceted connecting surface on either the housing or the locking cap or both. The multi-faceted connecting surfaces are configured to permit the bone mounting device to be mounted over a range of positions normal to, and over a range of rotational positions about, the shaft of the cam core member.

36 Claims, 3 Drawing Sheets

OTHER PUBLICATIONS

Moss, Excerpts from "Bone Screw With Adjustable Head", West Germany, 4 pages, date unknown.

Excerpts from "The TSRH Spinal Implant System", pp. 1–14, 16, date and author unknown.

Excerpts from "Modular Segmental Spinal–Instrumentation", West Germany, 4 pages, date and author unknown.

Acromed, Excerpts from "Isola Spinal System" (1991) Cleveland, Ohio, USA.

"Spinal Stability And Instability: Definitions, Classification, And General Principles Of Management", *The Unstable Spine*, by J. Frymoyer, et al., pp. 1–10 (1986).

Excerpts from "Materials Used In Spine Stabilization", Malinin, et al., pp. 30–32 date unknown.

"Current Concepts Of Internal Fixation", *The Unstable Spine*, by A. Kahn, III, pp. 45–83 (1986).

"Surgical Stabilization In Cervical Spine Trauma", *The Spinal Cord Injured Patient: Comprehensive Management*, by D.A. Capen, M.D. (1991) pp. 176–182.

"Anatomic And Technical Considerations Of Pedical Screw Fixation", *Clinical Orthopaedics and Related Research*, by J.N. Weinstein, D.O., et al., pp. 34–46 (Nov. 1992).

"The Use Of Intrapedicular Fixation Systems In The Treatment Of Thoracolumbar And Lumbosacral Fractures", *Orthopedics*, by M. Zindrick, et al., pp. 337–341 (Mar. 1992).

"A Biomechanical Analysis Of Zielke, Kaneda, And Cotrel–Dubousset Instrumentations In Thoracolumbar Scoliosis", *Spine*, by Y. Shono, et al., pp. 1305–1311 (Nov. 1991).

"Experimental Evaluation of Seven Different Spinal Fracture Internal Fixation Devices Using Nonfailure Stability Testing", *Spine*, by R.W. Gaines, Jr. et al., pp. 902–909 (Aug. 1991).

"Triangulation Of Pedicular Instrumentaion", *Spine*, by C.M. Ruland, et al., pp. S270–S276 (Jun. 1991).

"The Role Of Transpedicular Fixation Systems For Stabilization Of The Lumbar Spine", *Orthopedic Clinics of North America*, by M.R. Zindrick, pp. 333–344 (Apr. 1991).

"A Pedicle Screw Bridging Device For Posterior Segmental Fixation Of The Spine: Preliminary Mechanical Testing Results", *Journal of Biomedical Engineering*, by A.T. Rahmatalla, et al., pp. 97–102 (Mar. 1991).

"Long–Term Lumbar Facet Joint Changes In Spinal Fracture Patients Treated With Harrington Rods", *Spine*, by V.O. Gardner, et al., pp. 479–484 (Jun. 1990).

"Anterior Kostuik–Harrington Distraction Systems For The Treatment Of Kyphotic Deformities", *Spine*, by J.P. Kostuik, pp. 169–180 (Mar. 1990).

"Biomechanical Analysis Of Pedicle Screw Instrumentation Systems In A Corpectomy Model", *Spine*, by R. Ashman, et al., pp. 1398–1405 (Dec. 1989).

"Biomechanical Analysis Of Posterior Instrumentation Systems After Decompressive Laminectomy", *Jounal of Bone and Joint Surgery*, K.R. Gurr. pp. 680–691 (Jun. 1988).

"The Role Of Harrington Instrumentation And Posterior Spine Fusion In The Management Of Adolescent Idiopathic Scoliosis", *Orthopedic Clinics of North America*, by T.S. Renshaw, pp. 257–267 (Apr. 1988).

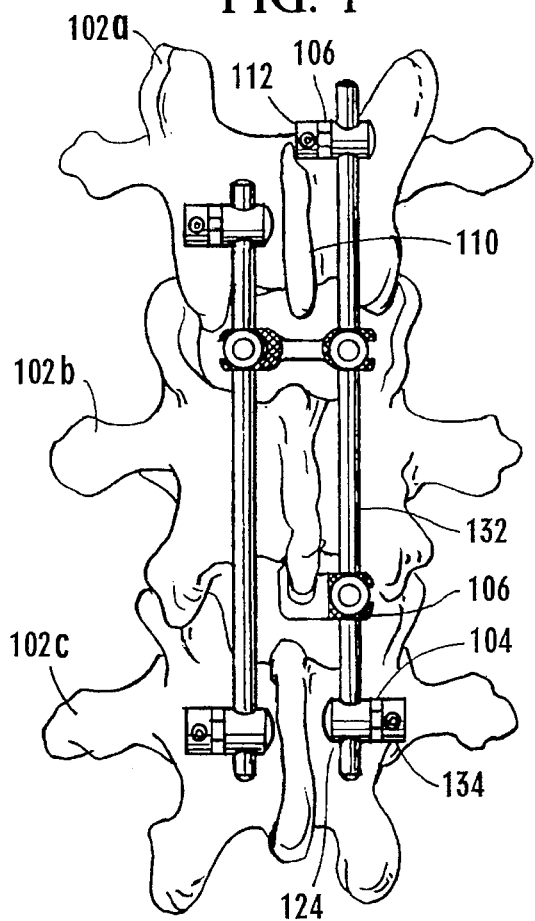
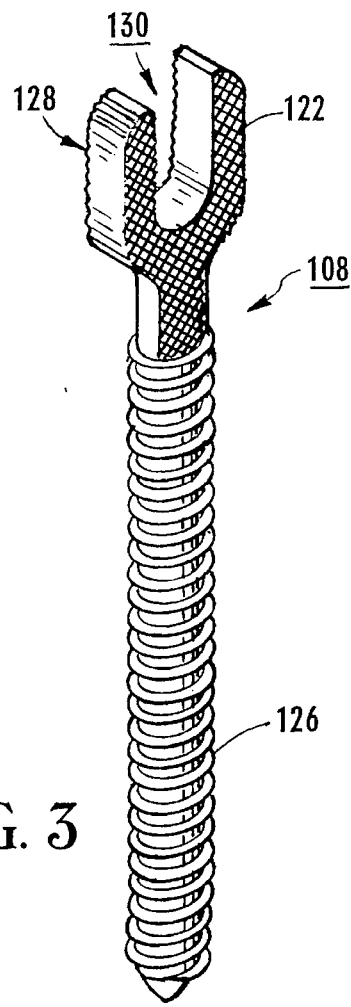
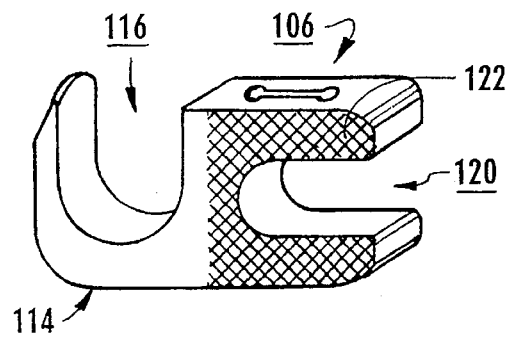
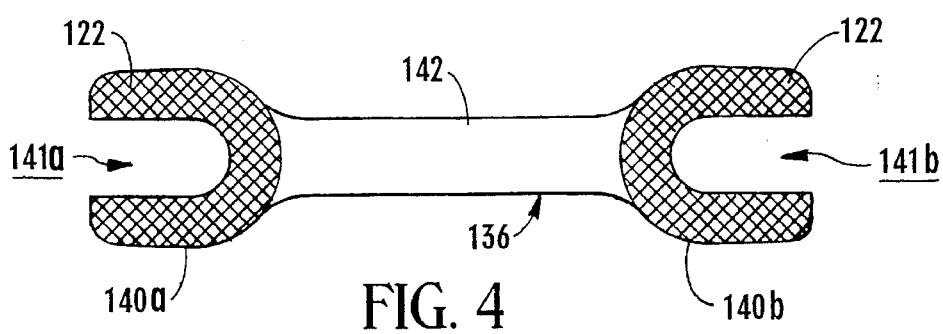

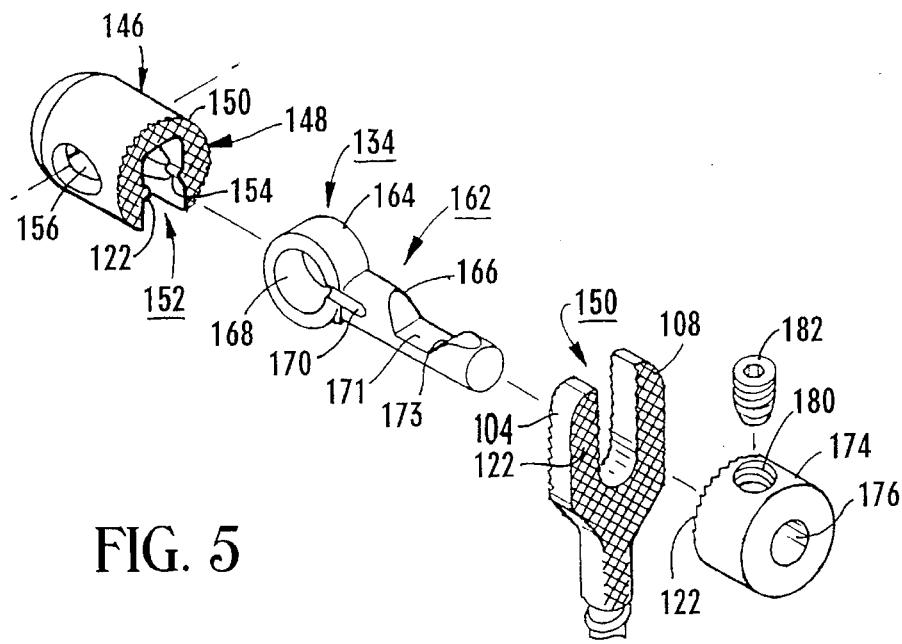
FIG. 5
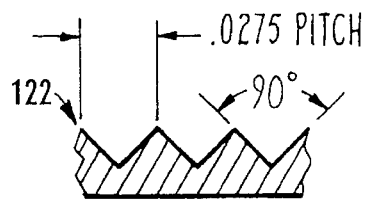
FIG. 6A
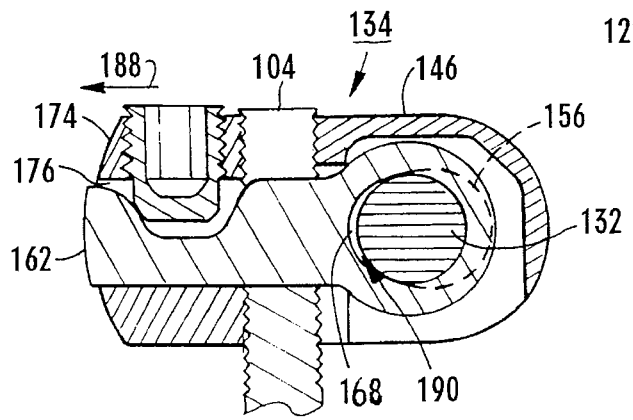
FIG. 8
FIG. 6B

SPINAL FIXATION SYSTEM

BACKGROUND OF THE INVENTION

1. Field of the Invention

The present invention generally relates to systems for securing portions of a patient's spinal column into a desired fixed position to correct injuries and defects and, more particularly, is concerned with a spinal fixation system which is adjustable when implanted and is resistant coming apart or detached from the patient's spine after implantation due to the patient's movement.

2. Description of the Related Art

Spinal fixation systems have been used for some time to secure sections of the spinal column, individual vertebral bodies and the like, into a fixed position to correct spinal injuries and defects. For example, spinal fixation systems have been used to correct injuries to the spine where an individual vertebral body has been shifted either laterally or vertically from its desired position.

Typically, in these applications, spinal fixation systems include a screw or hook which is attached to a portion of the vertebral body. At least one screw is attached to a first vertebral body which is in a correct position and is positioned on one side of the incorrectly positioned vertebral body. At least one screw or hook is then attached to a second correctly positioned vertebral body which is positioned on the other side of the incorrectly positioned vertebral body. Rods are then shaped so that they interconnect the hooks or screws in the first and second correctly positioned vertebral bodies. The surgeon then moves the incorrectly positioned vertebral body into a desired position, inserts a hook or screw and connects the hook or screw to the support rod so that the incorrectly positioned vertebral body is retained in its desired position.

One difficulty that spinal fixation systems must be able to overcome is the tremendous amount of forces that are exerted on the system once the system is implanted into a patient. As can be appreciated, the continuous movement of the patient's back during the average day exerts enormous forces against the spinal fixation system. This requires the spinal fixation system to be both securely fastened together and securely attached to the vertebral bodies.

A further difficulty associated with spinal fixation systems is that major surgery is required to install the system. This surgery includes the dissection of the patient's back until the affected vertebral bodies are exposed and then installation of the spinal fixation system. It is desirable to minimize the amount of time that the vertebral bodies are exposed. Unfortunately, however, installation of most prior art spinal fixation systems is time consuming which increases the risks associated with major surgery of this type.

Specifically, to implant the spinal fixation system, the screws or hooks must be attached to the various vertebral bodies. Subsequently, these screws or hooks must be connected to the support rods. However, the support rods typically have to be bent into required shape to be connect to the screws and hooks. Since the screws and hooks cannot be moved once they are attached to the vertebral bodies, the rods generally have to be bent to a specific shape before they are attached to the screws and hooks. This bending is normally done during surgery, while the vertebral bodies are accessible to the surgeon. This is due to the fact that the surgeon must adjust the bend of the rods in a trial and error manner until the system aligns the bodies as desired. Consequently, much time is expended during the course of the surgery shaping the rods to the exact tolerances needed to attach the screws and hooks to the rod.

To minimize the amount of time expended in shaping the rods, efforts have previously been made to develop an adjustable spinal fixation system. For example, U.S. Pat. No. 5,261,909 to Sutterlin et al. discloses a variable angle screw for a spinal implant system which reduces the amount of shaping that must be done with the rods when implanting a spinal fixation system. Sutterlin et al., discloses a bone screw which is yolked on the top to permit top loading and which has a plurality of radially extending splines. The bone screw is positioned in the vertebral body in a well known fashion and it is attached to the rod in the following manner.

The rod is inserted into an eyebolt assembly and the rod and eyebolt assembly is positioned adjacent the bone screw. A washer having two grooves on one side is then positioned around a shaft of the eyebolt, adjacent the rod, so that the rod rests in the grooves. The side of the washer opposite the rod has a plurality of radially extending splines which mate with the splines on the bone screw when the eyebolt and rod assembly is positioned adjacent the bone screw. A nut is then positioned on the shaft of the eyebolt and, when tightened, the nut urges the bone screw splines into the washer splines and also urges the washer to clamp the rod against the eyebolt.

The radially extending splines allow the surgeon to rotate the eyebolt with respect to the rod during attachment of the fixation system to the vertebral bodies. Thus, the surgeon may interconnect the bone screw and the support rods without having to shape the rod so that the eyebolt is exactly perpendicular to the bone screw at the point of attachment.

However, the bone screw assembly disclosed in the Sutterlin, et al. reference still requires the surgeon to shape the rod to ensure that the support rod is vertically aligned with the yoke of the bone screw. Specifically, the support rod must be shaped so that, at the point of attachment, the rod is the same distance from the vertebral body as the splined portion of the bone screw to permit the radially splined washer to align and interconnect with the radially splined portion of the eyebolt. Hence, the surgeon still has to spend valuable time shaping the support rods during the surgical procedure so that the fixation system can be properly implanted.

A further problem with the Sutterlin device is that, when the bone screw is attached to the rod, the rod is held in position only by virtue of the grooves clamping the rod to the interior surface of the eyebolt. If enough force is exerted on the rod, the rod can be induced to rotate in the grooves. Motion of the spine during normal human activities, e.g., walking, turning from side to side etc., can result in tremendous forces being exerted on an implanted spinal fixation system. These forces can be strong enough to induce the support rod to rotate or twist which may result in misalignment of other components, pressure on the spinal column, or damage to the components of the implanted spinal fixation system.

Still another problem with the Sutterlin spinal fixation device is that during installation, the surgeon has to be able to access the nut from the side to tighten and connect the bone screw to the rod. This requires the surgeon to make a larger incision to allow side access to the nut by a wrench. Further, the surgeon can have difficulty in tightening the nut using a wrench in the confined spaces adjacent the vertebral body, and this can result in a longer operation with increased risk to the patient.

For these reasons there is a need in the art for an improved spinal fixation system which is configured so that bone mounting devices, such as hooks and screws, which are attached to the vertebral bodies can be securely connected to a rod assembly with no or minimal bending of the rod and without requiring exact rotational or vertical alignment between the bone mounting devices and the rod assembly. Further, there is a need for an improved spinal fixation system which can be configured to prevent rotation or movement of the implanted rods due to movement of the patient. Finally, there is also a need in the art for an improved spinal fixation system which can be both directly implanted through a minimal incision, and also tightened without increasing incision size for such tightening to further minimize the amount of time, effort and trauma needed to implant the system.

SUMMARY OF THE INVENTION

The aforementioned needs are satisfied by the bone fixation system of the present invention which is essentially comprised of one or more bone mounting devices which can be attached to bone structures in a patient, at least one support rod and an attachment assembly which securely interconnect the bone mounting devices and support rod the system permits both rotation and lateral adjustment of the bone screw with respect to the rod during implantation, so the system can be configured to interconnect the vertebral members in a desired relationship, with little or no bending of the rod being necessary.

In one preferred embodiment of the present invention, a multifaceted surface comprised, for example, of a crosshatch pattern of individual elements, such as pyramids, is formed on a connecting surface of the bone mounting device that interconnects with other members of the fixation system. Further, a matching crosshatch pattern of elements is formed on a connecting surface of the attachment assembly so that the connecting surface of the bone mounting device can interlock with the connecting surface of the attachment assembly and prevent relative movement between the bone mounting device and attachment assembly.

The bone mounting device is also open yolked at the end adjacent the connecting surface. This allows a surgeon who is implanting the bone fixation system onto vertebral bodies in a patient to connect the bone mounting device to the other members of the bone fixation system by placing the other elements in the yolked portion of the bone mounting device. Further, the crosshatch and connecting surfaces on the attachment assembly and the bone mounting device allow the bone mounting device to be securely attached to the attachment assembly in a selected one of numerous rotational and lateral orientations between the bone mounting device and the attachment assembly.

The attachment assembly includes a housing having two openings for extending a support rod therethrough. A cam core member having an eyebolt shaped end is positioned in the housing so that the eye is aligned with the two openings such that the rod can extend through the two openings and the eye of the cam core member. The cam core member also has a shaft which extends out of the housing, and upon which a bone mounting device is positioned. A locking cap is also positioned on the shaft such that when it is locked or tightened, the cap is pressed against the bone mounting device, which itself is pressed against the housing, and is thereby secured to the attachment assembly. The tightening of the cap also causes the shaft to be pulled outward from the housing since the cap is pulling against the shaft as it presses the bone mounting device against the housing. As the shaft is pulled outwardly from the housing, the eye pulls the rod, which extends therethrough, against the two openings in the housing, thereby securing the rod within the housing. Thus, the attachment assembly is secured to the rod.

In one preferred embodiment of the attachment assembly, the housing contains a connecting surface and, when the locking cap is tightened, the connecting surface of the bone mounting device is urged against the connecting surface of the locking mechanism. The open yolk configuration of the bone mounting device permits the bone mounting device to be both vertically positioned relative to, and rotated about, the shaft of the cam core member. Further, once the bone mounting device is in its desired position about the shaft, with the locking cap tightened, the connecting surfaces provide secure attachment between the housing and the bone mounting device.

In another aspect of the attachment assembly, the openings in the housing are shaped so that when the locking cap is tightened, the cam core member urges the rod into a smaller diameter section of the openings in the housing. When the locking cap is fully tightened, the rod is crimped by the smaller diameter section of the opening which inhibits later rotation of the support rod due to forces exerted on different sections of the rod resulting from subsequent movement by the patient.

In another aspect of the attachment assembly, the cam core shaft has a beveled notch and the locking cap includes a set screw. The locking cap is positioned on the cam core shaft such that the set screw is positioned adjacent one beveled side of the notch. When the set screw is tightened, thereby locking the locking cap, the screw interacts with the beveled side to force the cam core member in a direction which urges the rod into the smaller diameter section of the opening in the housing. Tightening the set screw also urges the cam core member to move such that the bone mounting device is securely clamped between the housing and the locking cap, with the connecting surface on the bone mounting device interlocking with the connecting surface on the attachment assembly. Further, the attachment mechanism is preferably positioned relative the vertebral bodies of the patients spine so that the set screw is positioned exposed on the upper surface of the locking mechanism when the surgeon is tightening the set screw. This minimizes both the amount of time and the size of the incision needed to implant the bone fixation system of the present invention.

These and other objects and features of the present invention will become more fully apparent from the following description and appended claims taken in conjunction with the accompanying drawings.

BRIEF DESCRIPTION OF THE DRAWINGS

FIG. 1 is a top view of the spinal fixation system of the present invention implanted on three representative vertebral bodies of a patient's spine;

FIG. 2 is a perspective view of hook type of bone mounting device used with the spinal fixation system of the present invention;

FIG. 3 is a perspective view of a bone screw type of bone mounting device used with the spinal fixation system of the present invention;

FIG. 4 is a side view of one preferred embodiment of a bridge connector which is used to connect two rods of the spinal fixation system of the present invention;

FIG. 5 is an exploded perspective view of an attachment assembly of the spinal fixation system of the present invention used to interconnect a bone mounting device to a rod;

FIG. 6A, is a partial side view of a representative multifaceted connecting surface of either a bone mounting device or the attachment assembly of the present invention.

FIG. 6B is a front perspective view of the multifaceted connecting surface shown in FIG. 6A.

FIG. 8 is a sectional view of the attachment mechanism of the present invention, taken along lines 8—8 of FIG. 7 and illustrating the operation of the attachment assembly.

DETAILED DESCRIPTION OF THE PREFERRED EMBODIMENTS

Figure 7:
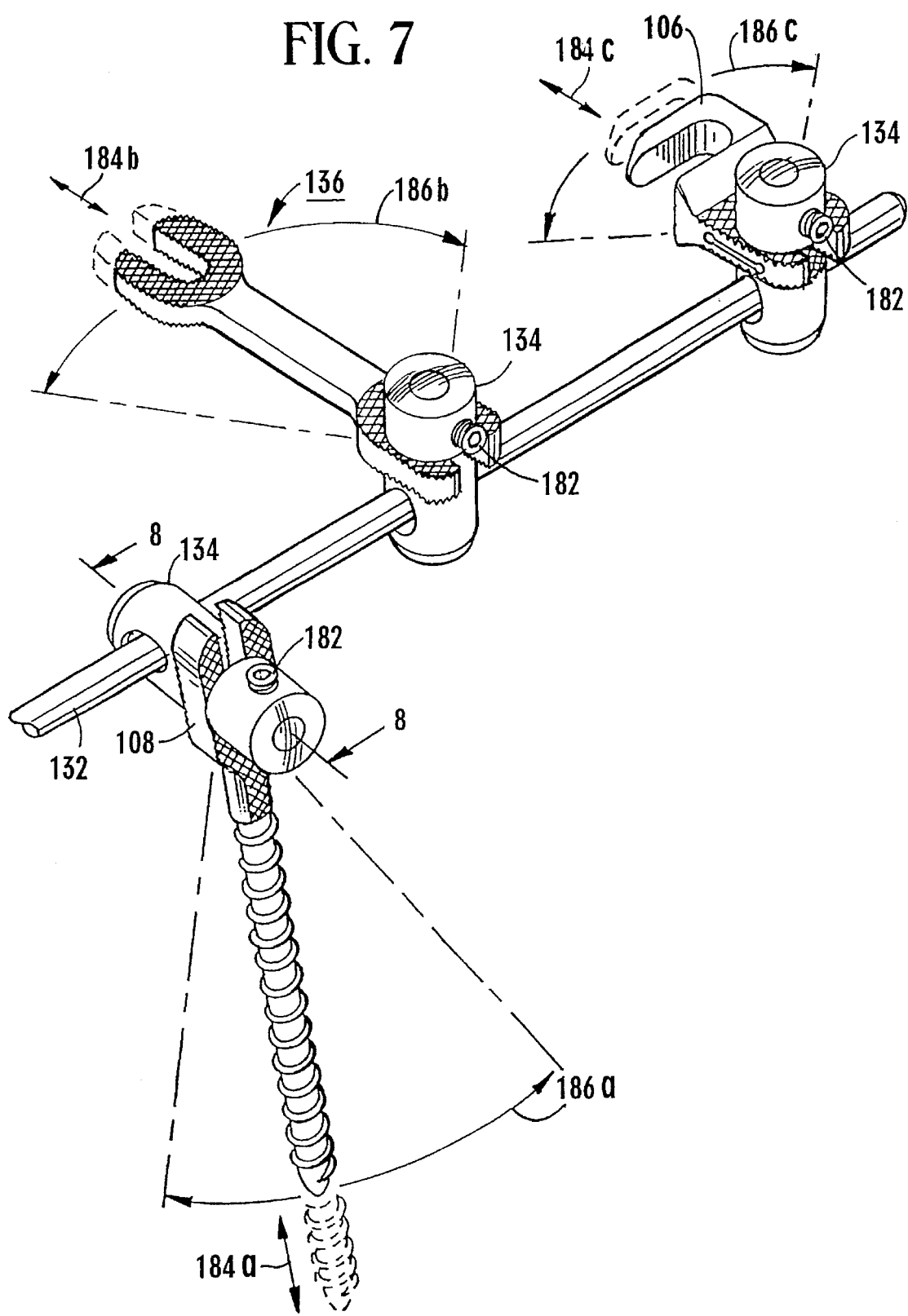
FIG. 7 is a partial perspective view of the spinal fixation system of the present invention illustrating two different types of bone mounting devices and the bridge connector attached to a support rod.

Reference will now be made to the drawings wherein like numerals refer to like parts. FIG. 1 illustrates one preferred embodiment of a spinal fixation system 100 of the present invention as implanted on three vertebral bodies 102a, 102b and 102c of a patient's spine. The spinal fixation system 100 is implanted using well known surgical procedures onto the vertebral bodies 102 to correct deformities of the spine resulting from injury or defect. Typically, the spinal fixation system 100 is used to correct spinal deformities where one or more vertebral bodies 102 has become displaced from its normal position and is thereby exerting pressure on spinal membranes, muscles or nerves. In particular, the spinal fixation system 100 can be used to reposition a vertebral body 102 which has moved longitudinally or laterally from its correct position in the spinal column. However, a person skilled in the art can appreciate that the spinal fixation system can be used for numerous other purposes and even adapted for use on membranes and bones other than human vertebral bodies.

The spinal fixation system 100 of the preferred embodiment shown in FIG. 1 includes several bone mounting devices 104 which are typically fixedly connected to the vertebral bodies 102. These bone mounting devices 104 include a hook 106 (FIG. 2) and a bone screw 108 (FIG. 3). The hooks 106 can be configured to be attached to the vertical part 110 of the vertebral body 102 or the laminar section 112 of the vertebral body 102. A typical hook 106 is more specifically illustrated in FIG. 2. The hook 106 is generally rectangular in shape with a foot portion 114 which defines an indentation 116 that is configured to hook around a portion of a vertebral body 102, e.g., the vertical portion 110 or the laminar section 112. In the embodiment shown in FIG. 2, the indentation 116 comprises a substantial portion of the foot portion 114 of the hook 106. Further, the hook 106 includes a mounting indentation 120 preferably extending lengthwise into the body of the hook 106 at the end opposite the foot portion 114. The mounting indentation 106 preferably defines a mounting location or mounting point where the hook 106 is interconnected with the rest of the spinal fixation system 100 in the manner that will be described below. The two lateral sides of the hook 106 (one shown in FIG. 2) preferably have a multifaceted connecting surface 122 adjacent the mounting indentation 120. The multifaceted connecting surface 122 may define a crosshatch configuration on the surface 122 in the manner described in greater detail with reference to FIGS. 6A and 6B below.

The other type of bone mounting device 104 in this preferred embodiment, the bone screw 108, is typically screwed into a pedicle portion 124 (FIG. 1) of the vertebral body 102 using well known surgical techniques. The bone screw 108 is shown more specifically in FIG. 3. The bone screw 108 generally consists of a threaded shaft 126 and a head 128. In this preferred embodiment, the head 128 is in the form of a Y-shaped yolk having a substantially U-shaped mounting indentation 130 extending axially into the head 128 of the screw 108. The mounting indentation 130 preferably defines a mounting location or mounting point for the bone screw 108 when the bone screw 108 is interconnected with the rest of the spinal fixation system 100 in the manner that will be described below. In this preferred embodiment, the multifaceted connecting surface 122 (FIG. 6) is formed on both lateral sides of the head 128 of the bone screw 108.

Referring back to FIG. 1, it may be seen that the bone mounting devices 104, are connected to one or more support rods 132 via an attachment assembly generally indicated at 134. Ideally, the support rods 132 are configured such that when the bone mounting devices 104 are attached thereto via the attachment assemblies 134, one of the vertebral bodies 102 are retained in a desired location relative to the other vertebral bodies 102. For example, the bone mounting devices 104 are attached to a displaced vertebral body 102 and are also attached to one or more correctly positioned, vertical bodies 102. The incorrectly positioned vertebral body 102 is then moved into its desired shape and the connecting rods 132 are then connected to each of the bone mounting devices, via the attachment assemblies 134, so that the incorrectly positioned vertebral body 102 is retained in its desired position. In this preferred embodiment, the support rods 132, the bone mounting devices 104 and the attachment assembly 134 are preferably made of a titanium alloy which is strong and lightweight and also has good characteristics for magnetic resonance imaging (MRI) purposes.

FIG. 1 further illustrates that two support rods 132 may also be implanted along a patient's spine. It should be understood that the number and configuration of the support rods 132 and the bone mounting devices 104 is entirely dependent upon the injury or deformity that the spinal fixation system 100 is attempting to correct. In circumstances where two support rods 132 are being used to correct a spinal injury or deformity, it may be desirable to connect these support rods 132 using a bridge member 136. The bridge member 136 is shown in greater detail in FIG. 4. Essentially, the bridge member 136 includes two open ends 140a and 140b and a connecting shaft 142. Each of the open ends 140a and 140b include a mounting indentation 141a and 141b. Each open end 140a and 140b also has the multifaceted connecting surface 122 formed on both sides of the bridge member 136 adjacent the open ends 140a and 104b. The mounting indentations 141a and 141b preferably define two mounting locations or mounting points for the bridge member 136 where bridge member 136 is interconnected with the rest of the spinal fixation system 100 in the manner that will be described below. As can be appreciated, the bridge member 136 can be of different lengths depending upon the desired separation of the support rods 132. Preferably, the bridge member 136 is also configured to be attached to the support rods 132 using the attachment assembly 134, however, any other known method of interconnecting the bridge member 136 to the support rods 132 can also be used.

The spinal fixation system 100 shown in FIGS. 1–3 allows a surgeon to position a vertebral body 102 into a desired position relative the other vertebral bodies 102 by initially attaching a bone mounting device 104 to one or more vertebral bodies 102. The surgeon then attaches one or more support rods 134 to the bone mounting devices 104 which results in displaced vertebral bodies 102 being urged into a desired place. The surgeon can also maintain separation between two rods 132 for therapeutic purposes using a bridge member 136. In this fashion, the surgeon can correct any number of spinal defects or injuries.

FIG. 5 illustrates the components comprising the attachment assembly 134 in greater detail. In this preferred embodiment, the attachment assembly 134 is configured to permit the surgeon to securely interconnect the support rods 132 and the bone mounting devices 104 by providing both rotational and lateral displacement ability between the rods 132 and the mounting devices 104. This minimizes any bending of the rods 132 required to secure the rods 132 to the mounting devices 104 in a desired relationship.

The attachment assembly 134 includes a substantially cylindrical housing 146. The housing 146 is open at a first end 148. The first end 148 also includes an end surface 150 which lies in a plane substantially perpendicular to the longitudinal axis of the housing 146. Upon the end surface 150 are a plurality of multifaceted elements such as pyramids, preferably positioned e.g., alternatingly spaced apart in a checker-board fashion, to define a crosshatched surface such as the multifaceted connecting surface 122. The central position of the body of the housing 146 is generally hollow and defines a substantially rectangular opening 152. The opening 152 extends into the center of the housing 146. A retaining detent 154 (one shown) extends inwardly from the end surface 150 and parallel to the longitudinal axis of the housing 146 on each of the interior side walls of the rectangular opening 152. The housing 146 also includes two rounded openings 156 extending in vertical alignment through each of the sidewalls of the housing 146 (one shown) and being configured to receive the support rod 132 therethrough.

The attachment assembly 134 further includes a cam core member 162. The cam core member 162 comprises a circular eyebolt section 164 and a shaft 166. The eyebolt section 164 includes a circular opening 168 which has a diameter slightly greater than the diameter of the support rod 132. A channel 170, extending from the circular opening 168 along the shaft 166 (one shown) parallel to its longitudinal axis is formed on each side of the cam core member 162. The width of the eyebolt section 164 is preferably slightly greater than the spacing between the two retaining detents 154 so that, when the eyebolt section 164 is press fitted into the housing 146, the retaining detents 154 are notably received in the channels 170 to thereby retain the cam core member 162 in proper alignment in the housing 146 while allowing for movement of the cam core member 162 back and forth in the direction of the arrows 172. The shaft 166 preferably has a circular cross section and an indentation or notch 171 is formed on the top surface of the shaft 166. At least one sidewall 173 of the indentation 171 is beveled.

The bone mounting device 104 is preferably mounted about the shaft 166 of the cam core member 162 at a mounting position which is between the eyebolt section 164 and the indentation 171. In FIG. 5, the bone mounting device 104 shown is the bone screw 108 and the mounting indentation 130 is dimensioned to flushly fit around the shaft 166 of the cam core member 162. The mounting indentation 120 in the hook 106 and the open ends 140 of the bridge member 136 are also similarly dimensioned.

The attachment assembly 134 also includes a cylindrical locking cap 174 which has an axially extending opening 176 extending therethrough. The locking cap 174 and the opening 176 are preferably dimensioned so that the shaft 166 of the cam core member 162 extends through the opening 176 with the sides of the shaft substantially flush with the inner surface of the axial opening 176 (see, FIG. 8). In this preferred embodiment, a multifaceted connecting surface 122 is also formed on the end of the locking cap 174 that is closest to the housing 146 when the attachment assembly 134 is assembled. The locking cap 174 also includes a threaded opening 180 extending entirely through a side wall of the locking cap 174 so as to receive a set screw 182 therein which can be extended through the opening 180 to extend into the axial opening 176. The set screw 182 secures the locking cap 174 to the cam core member 162 and also secures the bone mounted device 104 to the cam core member 162 as will be explained below in greater detail by reference to FIG. 8.

FIGS. 6A and 6B illustrate the configuration of the multifaceted connecting surface 122 found on each of the bone mounting devices 104, the bridge member 136, the first end 148 of the attachment assembly housing 146 and the end of the locking cap 174. The multifaceted surface is comprised of a plurality of 90 degree teeth having a pitch of 0.0275 inches which preferably extend at a 45 degree angle from the vertical and horizontal axis of the surface. One preferred method for forming these teeth is to create a series of parallel grooves in the surface having the indicated pitch. More parallel grooves are then formed at a 90° angle from the first group of grooves, and intersecting those grooves. This forms a cross hatch design on the surface, and forms a plurality of pyramid shaped teeth. Of course, cross hatching need not be used, and the teeth could be formed in other configurations with respect to each other and at other pitches. All of these variations are considered to be within the scope of the invention described herein.

FIG. 6B illustrates the layout of the 90 degree teeth on the first end 148 of the housing 146 and this layout is typical of the layout of the teeth on the crosshatch surfaces 122 on each of the bone mounted devices 104, the bridge assembly 136 and the locking cap 174. The purpose of the multifaceted, crosshatched connecting surfaces 122 on each of these components is to allow the bone mounting devices 104 and the bridge member 136 to be securely attached to the support rods 132 via the attachment assembly 132 over a range of different relative positions between these devices and the support rods 132.

For example, FIG. 7 illustrates that when the attachment assembly 132 is assembled, the bone mounting device 104, e.g., the hook 106 or the bone screw 108, and the bridge member 136 are positioned on the shaft 166 of the cam core member 162 interposed between the locking cap 174 and the first end 148 of the housing 146. In this preferred embodiment, the hook 106, the bone screw 108 and the bridge assembly 136 each contain the multifaceted connecting surface 122 on both sides. These surfaces of these components come in contact with the multifaceted connecting surface 122 on both the locking cap 174 and the housing 146. When the attachment assembly 132 is assembled and tightened, the multifaceted connecting surface on the hook 106, the bone screw 108 and the bridge 136 interlock with the multifaceted connecting surfaces 122 on the lock screw 174 and the housing 146.

This interlocking of the multifaceted connecting surfaces 122 permit affixing of the adjacent members in a desired configuration. In particular, as illustrated in FIG. 7, each of the bone mounting devices 104 and the bridge member 136 can be moved both in a direction normal to the axis of the cam core member 162 and radially about the axis of the cam core member 162 prior to being secured into the desired position. Once the bone mounting device 104 or the bridge member 136 is in the desired position about the cam core member 162, the surgeon then tightens the set screw 182 to securely connect the bone mounting device 104 or the bridge member 136 in the desired position.

Preferably, the area of the bone mounting devices 104 and the bridge member 136 having the multifaceted connecting surface 122 extends in a direction normal to the axis of the attachment assembly 134 a greater distance than the area of the crosshatch surfaces 122 on the locking cap 174 and the housing 146. This permits the bone mounting devices 104 to be securely coupled to the attachment assembly 134 over a range of positions, e.g., in the direction of the arrows 184a, b, and c, extending perpendicular to the axis of the attachment assembly 134. Further, since the cam core member 162 is substantially cylindrical at the position where the bone mounting device 104 or the bridge assembly 136 is mounted, the bone mounting device 104 and the bridge assembly 136 can also be securely coupled to the cam core member 102 over a 360° range of rotational positions, e.g., in the direction of the arrows 186a, b, and c.

Once the bone mounting devices 104 or bridge member 136 are in a desired orientation relative the attachment assembly 134, the set screw 182 is tightened clamping the bone mounting device 104 and/or the bridge member 136 between the multifaceted connecting surfaces 122 on the locking cap 174 and the housing 146 respectively. The multifaceted connecting surfaces 122 on the bone mounting device 104 or bridge member 136 then interlock with the multifaceted connecting surface 122 on the housing 146 and the locking cap 174 which results in the bone mounting device 104 being fixedly connected to the attachment assembly 134 in the desired orientation. Consequently, the multifaceted connecting surfaces 122 on the bone mounting device 104, the bridge member 136 and the attachment assembly permit the surgeon to securely connect the bone mounting devices 104 and the bridge member 136 to the attachment assembly 134 even though the bone mounting devices 104 and the bridge member 136 are not perfectly aligned with the attachment assembly 134.

FIG. 8 is a sectional view of the spinal fixation system 100 taken along the lines 8—8 in FIG. 7 which more clearly illustrates how the bone mounting device 104 is securely interconnected with the support rods 132 via the attachment assembly 134. As shown, the support rod 132 extends through both the opening 156 in the housing 146 and the opening 168 in the eyebolt section 164 of the cam core member 162. The bone mounted device 104 is positioned on the cam core member 162, interposed between first face 150 of the housing 146 containing the multifaceted connecting surface 122 and the surface of the locking cap 174 which also contains the multifaceted connecting surface 122.

Once the bone mounting device 104 is positioned in its desired location, the set screw 182 is tightened. The locking cap 174 is advantageously configured so that when it is positioned on the end of the cam core member 162 and the set screw 182 is tightened, the bottom surface of the set screw 182 comes in contact with the beveled side 173 of the notch 171 in the cam core member 162. Since the side 173 is beveled inward, the downward motion of the set screw 182 urges the cam core member 162 into the axial opening 176 of the locking cap 174 in the direction of an arrow 188 and also urges the locking cap 174 in the opposite direction. Hence, tightening the set screw 182 results in the bone mounting device 104 being securely clamped between the multifaceted connecting surfaces 122 on the locking cap 174 and on the housing 146.

The outward motion of the cam core member 162 further urges the support rod 132 into a narrow section 190 of the openings 156 in the housing 146. As shown in FIG. 8, the openings 156 are roughly teardrop shaped having a narrow section 190 where the opening 156 is smaller than the diameter of the rod 132. Tightening the set screw 182 results in the rod 132 being forced into the narrow section 190 where the rod 132 is preferably slightly deformed. Hence, the rod 132 is preferably crimped into the narrow section 190 of the opening 156 which minimizes any tendency of the rod 132 to rotate due to the patient's movements after implantation of the spinal fixation system 100. In this fashion, the bone mounting device 104 is securely interconnected to the support rod 132 via the attachment assembly 134. The bridge member 136 is also preferably interconnected to the support rods 132 via the attachment assembly 134 in a similar fashion.

FIG. 8 illustrates the attachment assembly 134 in it's typical orientation as implanted in the spine of the patient where the bone mounting device 104 extends downward into the vertebral member 102 (FIG. 2). The set screw 182 is preferably positioned on the side of the locking cap 174 so that, when the surgeon implants the bone mounting device 104 and interconnects the bone mounting device 104 to the support rods 132, the set screw 182 is directly accessible to the surgeon. Generally, when the surgeon is implanting the bone fixation system 100 in the spine of a patient, the surgeon makes incisions which expose the vertical surfaces of the vertebral bodies 102 (FIG. 1).

The bone mounting devices 104 are then typically implanted on the top of the vertical surfaces of the vertebral bodies 102 so that, when they are attached to the support rods 132 using the attachment assemblies 134, the set screw 182 is on the top surface of the attachment assembly 134 from the perspective of the surgeon. Hence, the set screw 182 is positioned so that the surgeon can tighten the set screw 182 without having to make a larger incision to provide access to the set screw 182.

The bone fixation system 100 of the present invention is thus both easier to implant than the spinal fixation systems of the prior art and it also requires fewer incisions and less trauma to the patient to implant. Further, since the multifaceted connecting surfaces 122 permit the bone mounting members 104 to be connected to the attachment assembly 136 over both a range of different rotational orientations and a range of different positions normal to the axis of the attachment assembly 136, the need to shape the support rods 132 is minimized with the bone fixation system 100. This results in a shorter operation and less trauma to the patient.

The spinal fixation system 100 of the present invention is also configured so that, once the bone mounting devices 104 and the support rods 132 are interconnected, the support rod 132 is secured so that the tendency of the support rod 132 to rotate due to the movements of the patient is minimized. Hence, injuries to the patient and misalignment or damage to the components of the spinal fixation system 100 due to rotation of the support rods 132 is further minimized.

Although the foregoing description of the preferred embodiment of the present invention has shown, described and pointed out the fundamental novel features of the invention, it will be understood that various omissions, substitutions and changes in the form of the detail of the apparatus as illustrated, as well as the uses thereof, may be made by those skilled in the art, without departing from the spirit of the present invention.

What is claimed is:

1. A bone fixation system comprising:

a bone mounting device configured to be mounted on a bone in a patient, said bone mounting device having a first multi-faceted connecting surface and a mounting point wherein said bone mounting device, when mounted on a bone, extends in a first direction;

a support rod; and an attachment assembly having a locked and unlocked configuration for securely interconnecting said bone mounting device with said support rod, said attachment assembly including a member extending along a first axis, wherein said member defines a first mounting location for said support rod and a second mounting location for said bone mounting device, and said attachment assembly also including a second multi-faceted connecting surface positioned adjacent said second mounting location so that said first and said second connecting surfaces are relatively rotatable and translatable and interlock when said attachment assembly is in said locked configuration to securely retain said bone mounting device in one of a range of first rotational positions about said first axis and at one of a range of first translational positions relative to said member in said first direction.

2. The system of claim 1, wherein said bone mounting device is comprised of a bone screw, having a threaded section, and a head section wherein said first multi-faceted connecting surface is formed on said head section.

3. The system of claim 2, wherein said bone screw is configured to be mounted in a pedicle region of a vertebral body in said patient.

4. The system of claim 1, wherein said bone mounting device is comprised of a hook having a foot region which defines an indentation configured to hook around a portion of said bone.

5. The system of claim 4, wherein said hook is configured to be mounted around a laminar portion of a vertebral body in said patient.

6. The system of claim 4, wherein said hook is configured to be mounted around a vertical section of a vertebral body in said patient.

7. The system of claim 1, wherein said attachment assembly comprises:

a housing having two openings configured to receive said support rod therethrough;

a cam core member having an eyebolt opening and a shaft, said cam core member positioned in said housing so that when said support rod extends through said two openings in said housing, said support rod extends through said eyebolt opening and said shaft extends out of said housing and provides said second mounting location for said bone mounting device; and a locking cap having a locked and unlocked configuration positioned on said shaft wherein said second mounting location is interposed between said housing and said locking cap and wherein said locking cap, when in said locked configuration, is urged toward said housing so that said bone mounting device is clamped between said housing and said locking cap.

8. The system of claim 7, wherein said housing includes said second multi-faceted connecting surface on a surface adjacent said second mounting location of said bone mounting device.

9. The system of claim 8, wherein said bone mounting device further includes a third multi-faceted connecting surface on a surface adjacent said locking cap and said locking cap further includes a fourth multi-faceted connecting surface on a surface adjacent said third multi-faceted connecting surface so that when said locking cap is in said locked configuration, said first and second multi-faceted connecting surfaces and said third and fourth multi-faceted connecting surfaces respectively interlock.

10. The system of claim 7, wherein said openings in said housing are configured to prevent rotation of said support rod in said openings when said locking cap is in said locked configuration.

11. The system of claim 10, wherein said openings in said housing include a narrow section and said eyebolt opening of said cam core member urges said support rod into said narrow sections when said locking cap is in said locked configuration thereby crimping said support rod and preventing rotation of said support rod.

12. The system of claim 11, wherein said locking cap includes a set screw and an opening for said set screw so that when said set screw is tightened in said opening, it engages with said cam core member and thereby induces said locking cap into said locked configuration.

13. The system of claim 12, wherein said shaft of said cam core member includes a beveled notch positioned so that when said set screw is tightened, said set screw makes contact with said beveled notch and thereby urges said cam core member in a direction where said support rod is urged into said narrow sections of said openings in said housing, and so that said bone mounting device is clamped between said housing and said locking cap.

14. A bone fixation system comprising:

a bone mounting device having a first multi-faceted connecting surface configured to be mounted on a bone in a patient, wherein said bone mounting member, when mounted on a bone, extends in a first direction;

a support rod; and an attachment assembly interconnecting said bone mounting device and said support rod, said attachment assembly having a locked and an unlocked configuration and said attachment assembly including a member extending along a first axis wherein said member defines a first mounting position for said bone mounting device and a second mounting position for said support rod comprising an opening having a narrow section configured so that when said attachment assembly is in said locked configuration, said support rod is urged into said narrow section and rotation of said support rod in said opening is prevented and wherein said attachment assembly also includes a second multi-faceted connecting surface positioned adjacent said first mounting location so that said first and said second connecting surfaces interlock when said attachment assembly is in said locked configuration to securely retain said bone mounting device in one of a range of first rotational positions about said first axis and in one of a range of first translational positions relative to said member in said first direction.

15. The system of claim 14, wherein said attachment assembly defines an axis and said first and second multi-faceted connecting surfaces are configured to interlock and securely attach said bone mounting device to said attachment assembly over a range of positions normal to said axis and over a range of rotational positions about said axis.

16. The bone fixation system of claim 14, wherein said bone mounting device is comprised of a bone screw having a threaded section and a head section and said bone screw is configured to be mounted in the pedicle region of a vertebral body in said patient.

17. The bone fixation system of claim 14, wherein said bone mounting device is comprised of a hook having a foot region which defines an indentation configured to hook around a portion of a vertebral body in said patient.

18. The system of claim 14, wherein said attachment assembly is comprised of:
- a housing having two openings configured to receive said support rod therethrough;
- a cam core member having an eyebolt opening and a shaft, said cam core member positioned in said housing so that when said support rod extends through said two openings in said housing, said support rod extends through said eyebolt opening and said shaft extends out of said housing and provides said first mounting position for said bone mounting device; and
- a locking cap having a locked and unlocked configuration positioned on said shaft wherein said first mounting position for said bone mounting device is interposed between said housing and said locking cap and wherein said locking cap, when in said locked configuration, is urged toward said housing about said shaft so that said bone mounting device is clamped between said housing and said locking cap.

19. The system of claim 18, wherein said locking cap includes a set screw and an opening for said set screw so that when said set screw is tightened in said opening, said locking cap enters said locked configuration.

20. The system of claim 19, wherein said shaft of said cam core member includes a beveled notch positioned so that when said set screw is tightened, said set screw makes contact with said beveled notch and thereby urges said cam core member in a direction where said support rod is urged into said narrow sections of said openings in said housing, and where said bone mounting device is clamped between said housing and said locking cap.

21. A method of correcting the position of a vertebral body in a patient's body comprising the steps of:
- positioning a first bone mounting device having a first multi-faceted connecting surface on a first vertebral body so that said bone mounting device extends in a first direction; and
- attaching said first bone mounting device to a mounting location on a member defining a first axis of a first attachment assembly having a second mult-faceted connecting surface;
- orienting said first bone mounting device in one of a range of first rotational positions about said first axis;
- orientating said first bone mounting device in one of a range of first translational positions relative to said member in said first direction; and
- securing said first attachment assembly to said first bone mounting device so that said first and said second multi-faceted surfaces interlock so as to retain said first bone mounting device in said one of said range of first rotational positions and in said one of said range of first translational positions.

22. The method of claim 21, further comprising the steps of:
- positioning a second bone mounting device having a third multi-faceted connecting surface on a second vertebral body;
- attaching said second bone mounting device to a mounting location on a second attachment assembly so that said third multi-faceted connecting surface interlocks with a fourth multi-faceted connecting surface on said second attachment assembly;
- positioning a support rod in a mounting opening in said first attachment assembly; and
- positioning said support rod in a mounting opening in said second attachment assembly.

23. The method of claim 22, further comprising the steps of:
- urging said support rod into a narrow section in said mounting opening in said first attachment assembly to thereby prevent rotation of said support rod in said mounting opening; and
- urging said support rod into a narrow section in said mounting opening in said second attachment assembly to thereby prevent rotation of said support rod in said mounting opening.

24. The method of claim 22, wherein the step of positioning a first bone mounting device comprises positioning a hook bone mounting device around a laminar section of said vertebral body.

25. The method of claim 22, wherein the step of positioning a second bone mounting device comprises positioning a bone screw into a pedicle section of said vertebral body.

26. The method of claim 22, further comprising the steps of:
- positioning a third bone mounting device having a first multi-faceted connecting surface on a third vertebral body;
- attaching said third bone mounting device to a mounting location on a third attachment assembly so that said first multi-faceted connecting surface interlocks with a second multi-faceted connecting surface on said third attachment assembly;
- positioning said third vertebral body in a desired position relative said first and second vertebral bodies;
- positioning said support rod in a mounting opening in said third attachment assembly; and
- securing said support rod in said mounting opening in said third attachment assembly to thereby retain said third vertebral body in said desired position.

27. A bone fixation system comprising:
- a plurality of bone mounting devices configured to be mounted on a plurality of bones in a patient, each of said bone mounting devices having a first multi-faceted connecting surface adjacent a mounting point wherein each said bone mounting device, when mounted in said bone, extends in a first direction;
- a plurality of support rods;
- a bridge member for interconnecting two of said plurality of support rods, said bridge member having said first multi-faceted connecting surface adjacent two different mounting points on said bridge member wherein said bridge member extends in a second direction when interconnecting two of said plurality of support rods; and
- a plurality of attachment assemblies for securely interconnecting said bone mounting devices and said bridge member with at least one of said support rods, each of said attachment assemblies, having a locked configuration, and each of said attachment assemblies including a member extending along a first axis wherein said member defines a first mounting location for said support rods and a second mounting location for said bone mounting device or said bridge member wherein said bone mounting device or said bridge member is attached by said mounting points to said attachment assembly, and wherein said attachment assembly includes a second multi-faceted connecting surface positioned on said member so that said first and said second connecting surface interlocks when said attachment assembly is in said locked configuration to securely retain each said bone mounting device or said bridge member in one of a range of rotational positions about said first axis and at one of a range of translational positions relative to said member in either said first or said second directions respectively.

28. The system of claim 27, wherein each of said attachment assemblies defines an axis and said first and second multi-faceted connecting surfaces are configured to interlock and securely attach said bone mounting device or said bridge member to said attachment assemblies of a range of positions normal to said axis of said attachment assembly and over a range of rotational positions about said axis.

29. A bone fixation system comprising:
a bone mounting device configured to be mounted on a bone in a patient, said bone mounting device having a mounting point;
a support rod; and
a securing device for interconnecting said support rod and said bone mounting device wherein said securing device comprises:
a housing having two openings, defining a first mounting location for said support rod, which are configured to receive said support rod therethrough;
a cam core member having an eyebolt opening and a shaft, positioned in said housing so that when said support rod extends through said two openings in said housing, said support rod extends through said eyebolt opening and said shaft extends out of said housing and provides a second mounting location for said bone mounting device; and
a locking cap having a locked and unlocked configuration positioned on said shaft wherein said second mounting location is interposed between said housing and said locking cap and wherein said locking cap, when in said locked configuration, is urged toward said housing so that said bone mounting device is clamped between said housing and said locking cap.

30. The system of claim 29, wherein said bone mounting device is comprised of a bone screw having a threaded section and a head section wherein a first multi-faceted connecting surface is formed on said head section and said bone screw is configured to be mounted in a pedicle region of a vertebral body in said patient and wherein said securing device includes a second multi-faceted surface which engages with said first multi-faceted surface to securely interconnect said support rod and said bone mounting devices.

31. The system of claim 30, wherein said first and second multi-faceted surfaces are comprised of a plurality of multi-faceted elements projected from a base surface.

32. The system of claim 31, wherein said multi-faceted elements comprise a plurality of sides defining a pyramid configuration.

33. The system of claim 29, wherein said bone mounting device is comprised of a hook having a foot region defining an indentation configured to hook around a portion of a vertebral body in said patient.

34. The system of claim 29, wherein said openings in said housing include a narrow section and said eyebolt opening of said cam core member urges said support rod into said narrow sections when said locking cap is in said locked configuration thereby crimping said support rod and preventing rotation of said support rod.

35. A spinal fixation system comprising:
a bone mounting device configured to be mounted on a vertebral body in a patient, said bone mounting having a first multi-faceted connecting surface adjacent a mounting point;
a support rod;
a housing having two openings configured to receive said support rod therethrough said housing and a second multi-faceted surface;
a cam core member having an eyebolt opening and a shaft, said cam core member positioned in said housing so that when said support rod extends through said two openings in said housing and through said eyebolt opening, said shaft extends out of said housing and provides a first mounting location for said bone mounting device and wherein said shaft further includes a beveled notch; and
a locking cap positioned on said shaft, wherein said first mounting location is interposed between said surface of said housing having said second multi-faceted surface and said locking cap, said locking cap including a set screw and an opening for said set screw so that when said set screw is tightened in said opening, said set screw makes contact with said beveled notch and urges said cam core member in a direction such that said bone mounting member is clamped between said locking cap and said housing with said first and second multi-faceted surfaces interlocking.

36. The system of claim 35, wherein said openings in said housing include a narrow section and wherein tightening of said set screw further induces said cam core member to move so that said eye bolt section urges said support rod into said narrow section thereby preventing said support rod from rotating in said openings.

* * * * *